United States Patent
Harms et al.

(10) Patent No.: US 6,902,579 B2
(45) Date of Patent: Jun. 7, 2005

(54) LENGTHWISE ADJUSTABLE SPACE-MAINTAINER FOR INSERTING BETWEEN TWO VERTEBRAL BODIES

(75) Inventors: Jürgen Harms, Karlsruhe (DE); Lutz Biedermann, VS-Villingen (DE); Peter Ostermann, Berlin (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 0 days.

(21) Appl. No.: 10/034,545

(22) Filed: Dec. 21, 2001

(65) Prior Publication Data

US 2002/0082696 A1 Jun. 27, 2002

(30) Foreign Application Priority Data

Dec. 27, 2000 (DE) .......................................... 100 65 398

(51) Int. Cl.[7] .................................................. A61F 2/44
(52) U.S. Cl. .................................. 623/17.11; 623/17.15
(58) Field of Search .......................... 623/17.11, 17.15, 623/17.16, 17.12, 17.13, 17.14; 606/61

(56) References Cited

U.S. PATENT DOCUMENTS 5,702,455 A * 12/1997 Saggar ..................... 623/17.15
5,916,267 A * 6/1999 Tienboon ................. 623/17.11
5,989,290 A * 11/1999 Biedermann et al. ..... 623/17.11
6,176,881 B1 * 1/2001 Schar et al. ............. 623/17.11
6,193,755 B1 * 2/2001 Metz-Stavenhagen et al. ... 623/17.11
6,193,756 B1 * 2/2001 Studer et al. ............ 623/17.15
6,200,348 B1 * 3/2001 Biedermann et al. ..... 623/17.11
6,524,341 B2 * 2/2003 Lang et al. .............. 623/17.15

FOREIGN PATENT DOCUMENTS

| DE | G 91 01 603.7 | | 2/1991 | ............. A61F/2/44 |
| DE | 196 22 827 A1 | | 6/1996 | ............. A61F/2/44 |
| WO | WO 00/23013 | * | 4/2000 | ............. 623/17.15 |

* cited by examiner

*Primary Examiner*—Pedro Philogene
(74) *Attorney, Agent, or Firm*—Barley Snyder LLC

(57) ABSTRACT

A space-maintainer is created, which has a sleeve-shaped first part 1 and a second part 2 contained in this and displaceable in the axial direction relative to the first part. So that lengthwise adjustment is possible in a simple manner during the process of an operation, one of the parts has a toothed profile 22 extending parallel to the longitudinal axis of the parts and the other part has a toothed wheel 24 located in engagement with the toothed profile 22 for adjusting the total length.

7 Claims, 1 Drawing Sheet

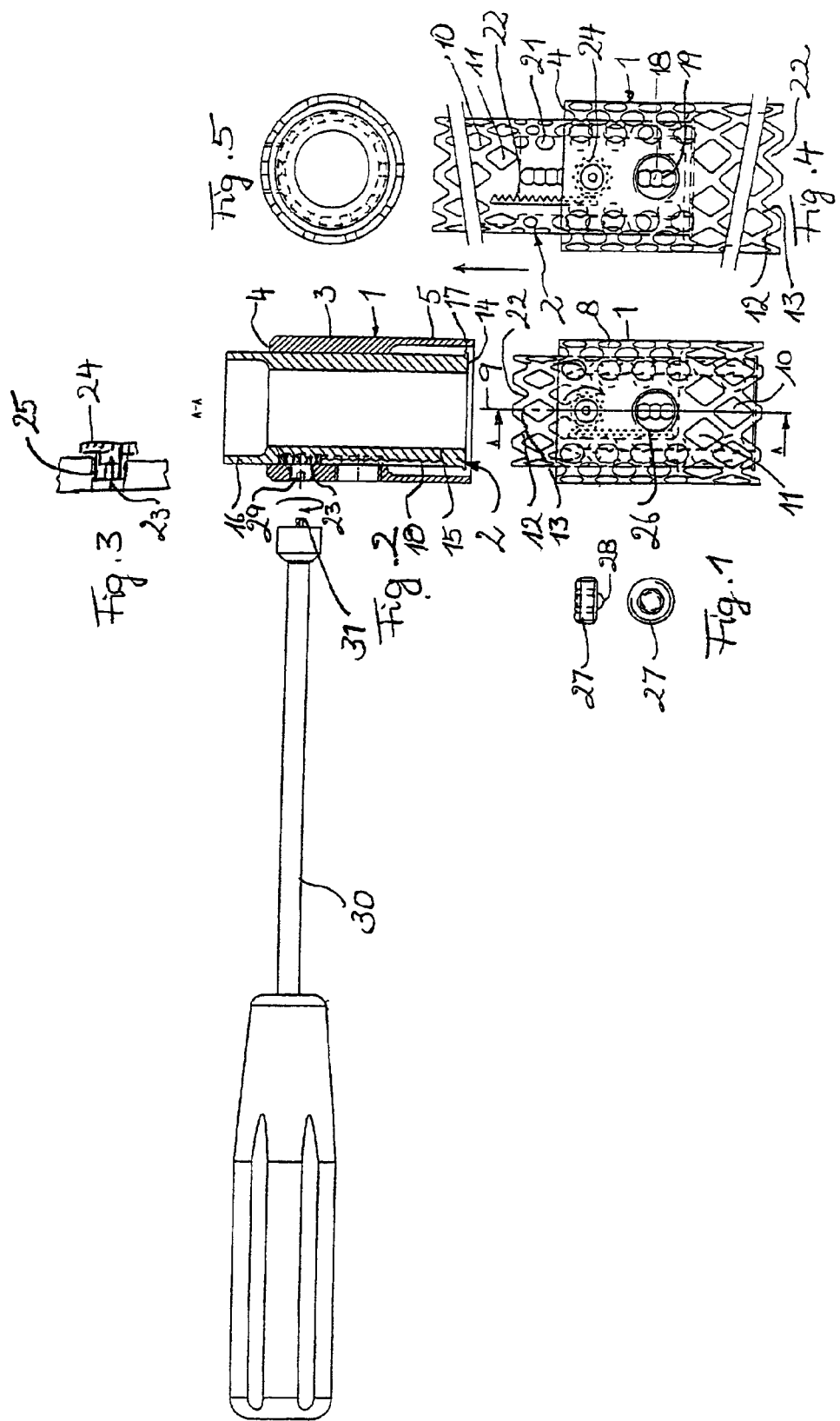

LENGTHWISE ADJUSTABLE SPACE-MAINTAINER FOR INSERTING BETWEEN TWO VERTEBRAL BODIES

The invention relates to a space-maintainer for inserting between to vertebral bodies.

A space-maintainer of this kind is known from EP 0 997 528-A. This known space-maintainer enables adjustment to the desired length by relative displacement of the two parts with respect to one another. From DE 196 22 827 A1 a space-maintainer is known with a sleeve-shaped first part and a second part guided therein and displaceable in the axial direction relative to the first part, said second part including a screw thread. Furthermore, a ring is provided which can be screwed on the screw thread, hence which is directly connected to the second part and forms a stop for the first part. By means of a force that acts on the ring and rotates the ring, the parts are moved in a direction relative to one another so that a change of length occurs. From U.S. Pat. No. 5,702,455 a space-maintainer is known including a first and a second sleeve. A third element is formed as a threaded cylinder on which the two sleeves can be screwed with an internal screw thread. The screw threads of the sleeves are formed to be opposed to each other. By rotating the central element including the exterior screw thread a displacement in the longitudinal direction occurs to the two sleeves with respect to each other.

The object of the invention is to create a space-maintainer of the kind initially described which is easier to adjust in length during the process of the operation.

In accord with the present invention, a space-maintainer for inserting between two vertebral bodies comprises a sleeve-shaped first part (1) and a second part (2) guided therein and displaceable in the axial direction relative to the first part, which are both (1, 2) connected to one another by a device which transforms a rotary movement acting from outside into a movement displacing the carts (1, 2) in their relative longitudinal position, wherein one of the parts has a toothed profile (22) extending parallel to the longitudinal axis of the parts and the other part has a toothed wheel (24) located in engagement with the toothed profile (22) for adjusting a total length.

Further developments of the invention are characterised in the subordinate claims.

Further features and advantages of the invention emerge from the description of an embodiment example using the figures.

FIG. 1 shows a side view of the space-maintainer.
FIG. 2 shows a section along the line A—A.
FIG. 3 shows a detail from FIG. 2.
FIG. 4 shows the side view as in FIG. 1 in an expanded state.
FIG. 5 shows a horizontal projection on to the device shown in FIG. 4.

As can best be seen from FIGS. 1 and 2, the outer sleeve 1 has a first casing section 3, extending from the first open end 4 over more than half the sleeve toward its other end. This casing section has a first inner diameter. In the second casing section 5 adjoining it the casing is fashioned as thinner on the inside and has a second inner diameter which is larger than the first inner diameter. The first casing section has a plurality of recesses 8, distributed over the entire casing section, in the form of bores extending through the casing. The second casing section 5, in the way seen in FIG. 1, has rhomboidal recesses 10, 11, extending with their longitudinal diagonal parallel to the casing axis 9. Bordering on the edge a first group of these rhomboidal recesses 10 extends in the circumferential direction and, adjoining them, directed towards the first open end 4 a second group 11, wherein the second group is offset from the first group in the axial direction by half the height of a rhombus. In this way a network of flat strips 12, 13, intersecting one another at an acute angle, is formed, inclined at angles of identical size in each case against the longitudinal diagonal of the rhombi. The size of the rhombi and the flat strips bordering on these is chosen in such a way that the number of rhombi is always a whole number in the circumferential direction. The thus formed edge therefore has prongs formed by the flat strips and indentations 22 in between. The sleeve-shaped second part 2 has a casing section 15, adjoining its first open end 14, with a first outer diameter. This casing section extends in the embodiment example shown over slightly more than two thirds of the axial length. A second casing section 16 with the same outer diameter, extending up to the second open end, adjoins it. The outer diameter is chosen in such a way that the inner sleeve 2 is contained so as to slide in the first casing portion 3 of the outer sleeve 1. On the first open end 14 the inner sleeve has an edge 17, the diameter of which is larger than the diameter of the first casing section and larger than the first inner diameter of the outer sleeve and smaller than the inner diameter of the second casing section 5 of the outer sleeve.

The first casing section 15 has in a direction parallel to the casing axis 9 a plurality of indentations 18 shaped like ball segments, directly bordering on one another, the depth of which is smaller than their radius. The distance in each case between two adjacent indentations is smaller than the diameter of the edge of the indentations shaped like ball segments bordering the indentation. It is therein achieved that the border 19 between two adjacent indentations is lower than the actual edge of the indentations themselves. The area of the indentations 18 extends over almost the entire length of the first casing section 15. In this first casing section, by analogy to the recesses 8, are arranged recesses 21, also extending over the entire surface of the casing section and formed as bores going through the casing. The second casing section 16 is constructed analogously to the second casing section 5 of the first sleeve and has rhomboidal recesses 10, 11 arranged in the same way, with the bands 12, 13 in between. The bands are constructed as running crosswise to one another on the open end of the sleeve and in each case enclose indentations 22 with relatively sharp edges projecting in between.

As can best be seen from FIGS. 2 and 4, the wall of the inner second part 2 has a toothed profile 22, extending parallel to the longitudinal axis 9, which is formed in the wall in such a way that a row of teeth emerges as with a toothed rack. At the same time the outer sleeve 1 has in the first casing section 3 a bore 23, which acts as pivot bearing. Further provided is a toothed wheel 24, which has a shaft 25 on one of its sides. The shaft 25 is dimensioned in such a way that it is carried in the bore 23 so as to slide. The bore 23 is arranged in the circumferential direction in such a way that the toothed wheel 24 carried therein is in engagement with the toothed profile 22 in the way seen best in FIGS. 1 and 4.

As can best be seen from FIGS. 1 and 4, the radius of the toothed wheel 24 is chosen in such a way that the centre of the toothed wheel carried in the bore 23 on engagement with the toothed profile 22 is located precisely on the centre line of the indentations 18.

As can best be seen from FIGS. 1 and 4, the bore 23 is attached close to the first open end 4 of the outer sleeve 1, wherein, however, the distance from the open end is at least equal to the diameter of the toothed wheel. At a distance from the bore 23 and, as can best be seen from FIG. 1, located on a line located parallel to the casing axis 9 with the centre of the bore 23, the outer sleeve 1 has a thread bore 26. Further provided is a fixing screw 27, shown in FIG. 1 at the bottom in horizontal projection and at the top in side view. The fixing screw has an outer thread, corresponding to the inner thread of the bore 26. On the front end of the fixing screw a ball segment 28 is provided. The dimensions of the ball segment correspond to the greater depth of the indentations 18.

As can be seen from FIG. 2, the shaft 25 of the toothed wheel 24 has an orifice 29 at its open end, which is shaped in such a way that a correspondingly matched rotary instrument or screwing instrument can be inserted. Further provided is a kind of screwdriver 30, which has a projection 31 on its front face corresponding to the shape of the orifice 29.

In operation the space-maintainer is first inserted in the telescoped way shown in FIG. 2 between two adjacent vertebral bodies. Then, by insertion of the screwdriver 30 with its projection into the orifice 29 and rotating, expansion of the space-maintainer to a desired length takes place. After the length has been reached, the fixing screw 27, which has possibly already been loosely inserted beforehand into the thread bore 26, is tightened, so a stable connection is produced between the two sleeve parts 1 and 2.

As indicated in FIG. 4, by the special construction of sections 5 and 16 of the sleeves by cutting off the edges a change in the inclination of the faces acting on the vertebrae can be brought about.

What is claimed is:

1. A space-maintainer for inserting between two vertebral bodies, said space maintainer comprising:

a sleeve-shaped first part having a longitudinal axis;

a second part guided therein, the second part being displaceable in an axial direction relative to the first part;

a device connecting the sleeve-shaped first part and the second part, the device comprising a first component having a toothed profile extending parallel to the longitudinal axis and a second component having a toothed wheel located for engagement with the toothed profile of the first component, the rotational axis of the toothed wheel being perpendicular to the toothed profile, wherein the first component is attached to one of the sleeve-shaped first part or second part and the second component is attached to the other of the sleeve-shaped first part or second part so that a rotary movement of the toothed wheel is converted into a movement displacing the second part relative to the sleeve-shaped first part in the axial direction for adjusting a total length of the sleeve-shaped first part and the second part.

2. The space-maintainer according to claim 1, wherein the toothed wheel is mounted in the sleeve-shaped first part.

3. The space-maintainer according to claim 1, wherein the second part further comprises an outer surface and a grid section, extending in the axial direction, the grid section comprising a grid structure consisting of a plurality of indentations arranged adjacent to one another in the axial direction on said outer surface facing the first part; and the space-maintainer further comprises a stopping part that cooperates with the grid structure.

4. The space maintainer according to claim 1, further comprising a rotary instrument, which can engage the toothed wheel for changing a rotary position of the toothed wheel and, therefore, the total length of the sleeve-shaped first part and the second part.

5. The space-maintainer according to claim 4, wherein the second part further comprises an outer surface and a grid section, extending in the axial direction, the grid section comprising a grid structure consisting of a plurality of indentations arranged adjacent to one another in the axial direction on said outer surface facing the first part; and the space-maintainer further comprises a stopping part that cooperates with the grid structure.

6. The space-maintainer according to claim 4, wherein the toothed wheel is mounted in the sleeve-shaped first part.

7. The space-maintainer according to claim 6, wherein the second part further comprises an outer surface and a grid section, extending in the axial direction, the grid section comprising a grid structure consisting of a plurality of indentations arranged adjacent to one another in the axial direction on said outer surface facing the first part; and the space-maintainer further comprises a stopping part that cooperates with the grid structure.

* * * * *

UNITED STATES PATENT AND TRADEMARK OFFICE
CERTIFICATE OF CORRECTION

PATENT NO.    : 6,902,579 B2
DATED         : June 7, 2005
INVENTOR(S)   : Jürgen Harms, Lutz Biedermann and Peter Ostermann It is certified that error appears in the above-identified patent and that said Letters Patent is hereby corrected as shown below:

Column 1,
Line 6, "to" should be changed to -- two --.
Line 4, add -- Field of the Invention --.
Between lines 6 and 7, add -- Background of the Invention --.
Between lines 27 and 28, add -- Summary of the Invention --.
Between lines 44 and 45, add -- Brief Description of the Drawings --.
Between lines 54 and 55, add -- Detailed Description of the Invention --.

Signed and Sealed this

Twenty-third Day of August, 2005

JON W. DUDAS
*Director of the United States Patent and Trademark Office*